United States Patent
Anthony et al.

(10) Patent No.: US 10,040,854 B2
(45) Date of Patent: Aug. 7, 2018

(54) ANTIBODIES AGAINST CD106 (VCAM-1)

(71) Applicant: Isis Innovation Limited, Oxford (GB)

(72) Inventors: Daniel Clive Anthony, Oxford (GB); Sandra Jane Campbell, Oxford (GB); Francis Joseph Carr, Balmedie (GB); Robin Patrick Choudhury, Oxford (GB); Benjamin Guy Davis, Oxford (GB); Timothy David Jones, Babraham (GB); Nicola Ruth Sibson, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 194 days.

(21) Appl. No.: 14/397,074

(22) PCT Filed: Apr. 24, 2013

(86) PCT No.: PCT/GB2013/051037
§ 371 (c)(1),
(2) Date: Oct. 24, 2014

(87) PCT Pub. No.: WO2013/160676
PCT Pub. Date: Oct. 31, 2013

(65) Prior Publication Data
US 2015/0125878 A1    May 7, 2015

(30) Foreign Application Priority Data
Apr. 24, 2012 (GB) .................................. 1207155.1

(51) Int. Cl.
| | | |
|---|---|---|
| *A61K 39/395* | (2006.01) | |
| *C07K 16/28* | (2006.01) | |
| *G01N 33/543* | (2006.01) | |
| *G01N 33/574* | (2006.01) | |
| *G01N 33/58* | (2006.01) | |
| *G01N 33/68* | (2006.01) | |

(52) U.S. Cl.
CPC ... *C07K 16/2836* (2013.01); *G01N 33/54346* (2013.01); *G01N 33/57492* (2013.01); *G01N 33/585* (2013.01); *G01N 33/6872* (2013.01); *G01N 33/6896* (2013.01); *C07K 2317/92* (2013.01); *G01N 2333/70542* (2013.01); *G01N 2800/285* (2013.01)

(58) Field of Classification Search
None
See application file for complete search history.

(56) References Cited

U.S. PATENT DOCUMENTS

| | | |
|---|---|---|
| 6,307,025 B1 | 10/2001 | Hession et al. |
| 7,655,417 B2 | 2/2010 | Chung et al. |
| 2003/0153731 A1 | 8/2003 | Hession et al. |
| 2012/0251443 A1* | 10/2012 | Ozaki ................ A61K 49/1896 424/1.65 |

FOREIGN PATENT DOCUMENTS

| | | |
|---|---|---|
| WO | WO-9314220 A1 | 7/1993 |
| WO | WO-2007139359 A1 | 12/2007 |
| WO | WO-2010114312 A2 | 10/2010 |

OTHER PUBLICATIONS

Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Allen et al, "Endothelial Expression of VCAM-1 in Experimental Crescentic Nephritis and Effect of Antibodies to Very late Antigen-4 or VCAM-1 on Glomerular Injury", (1999) J. Immunol., 162:9, 5519-5527.
Carter et al, "Vascular cell adhesion molecule-1 (VCAM-1) blockade in collagen-induced arthritis reduces joint involvement and alters B cell trafficking", (2002) Clin. Exp. Immunol., vol. 128, pp. 44-51.
Chen et al, "VCAM-1 blockade delays disease onset, reduces disease severity and inflammatory cells in an atopic dermatitis model", (2010) Immunol. Cell Biol., vol. 88, pp. 334-342.
Dako, "Specification Sheet, Monoclonal Mouse Anti-Human VCAM-1", <http://www.finels.com/product/up_files/M7106.pdf> Retrieved on Jul. 9, 2013, 2 pages.
Frenette et al, "Endothelial selectins and vascular cell adhesion molecule-1 promote hematopoietic progenitor homing to bone marrow", (1998) Proc. Natl. Acad. Sci. USA, vol. 95, 14423-14428.
Gao et al, "Expression of VCAM-1 and VLA-4 dependent T-lymphocyte adhesion to dermal fibroblasts stimulated with proinflammatory cytokines", (1996) Immunology, vol. 89, pp. 375-383.
Gorcyznski et al, "Manipulation of skin graft rejection in alloimmune mice by anti-VCAM-1:VLA-4 but not anti-ICAM-1:LFA-1 monoclonal antibodies", (1995) Transpl. Immunol., No. 3, pp. 55-61.
Konstantopoulos et al, "Endothelial P-selectin and VCAM-1 each can function as primary adhesive mechanisms for T cells under conditions of flow", (1997) J. Leukoc. Biol., vol. 61, pp. 179-187.
McAteer et al, "In vivo magnetic resonance imaging of acute brain inflammation using microparticles of iron oxide", (2007) Nature Medicine, 13:10, pp. 1253-1258.

(Continued)

*Primary Examiner* — Phillip Gambel
(74) *Attorney, Agent, or Firm* — Norton Rose Fulbright US LLP

(57) ABSTRACT

The invention provides an antibody or fragment thereof that specifically binds to human endothelial vascular cell adhesion molecule-1 (VCAM-1), wherein the antibody or fragment thereof binds to the extracellular domain of VCAM-1, and wherein the antibody or fragment thereof binds to VCAM-1 when expressed on endothelial cells, wherein the antibody or fragment thereof is a human or humanized antibody, or fragment thereof.

14 Claims, 1 Drawing Sheet

(56) References Cited

OTHER PUBLICATIONS

Muschel et al, "MRS-AACR Joint Conference on Metastasis 2010", (2011) Clin. Exp. Metast., vol. 28, p. 162.
Okada et al, "Significance of VLA-4-VCAM-1 interaction and CD44 for transendothelial invasion in a bone marrow metastatic myeloma model", (1999) Clin. Exp. Metastasis, No. 17, pp. 623-629.
Osborn et al, "Activated Endothelium Binds Lymphocytes Through a Novel Binding Site in the Alternately Spliced Domain of Vascular Cell Adhesion Molecule-1", (1992) J. Exp. Med., vol. 176, pp. 99-107.
Schweitzer et al, "Constitutive Expression of E-Selectin and Vascular Cell Adhesion Molecule-1 on Endothelial Cells of Hematopoietic Tissues", (1996) Am. J. Pathol., 148:1, pp. 165-175.
Serres et al, "VCAM-1-targeted magnetic resonance imaging reveals subclinical disease in a mouse model of multiple sclerosis", (2011) FASEB J., vol. 25, pp. 4415-4422.
Serres et al, "Molecular MRI enables early and sensitive detection of brain metastases", (2012) PNAS, 109:17, pp. 6674-6679.
Slack-Davis et al, "Vascular Cell Adhesion Molecule-1 Is a Regulator of Ovarian Cancer Peritoneal Metastasis", (2009) Cancer Res., vol. 69, pp. 1469-1476.
Soriano et al, "VCAM-1, but Not ICAM-1 or MAdCAM-1, Immunoblockade Ameliorates DSS-Induced Colitis in Mice", (2000) Lab. Invest., vol. 80, pp. 1541-1551.
Stegall et al, "α4 Integrin in Islet Allograft Rejection", (2001) Transplantation, vol. 71, pp. 1549-1555.
Vonderheide et al, "Residues Within a Conserved Amino Acid Motif of Domains 1 and 4 of VCAM-1 Are Required for Binding to VLA-4", (1994) The Journal of Cell Biology, vol. 125, No. 1, pp. 215-222.
Wellicome et al, "A Monoclonal Antibody That Detects a Novel Antigen on Endothelial Cells That Is Induced by Tumor Necrosis Factor IL-1, or Lipopolysaccharide", (1990) The Journal of Immunology, The American Association of Immunologists, US, vol. 144, No. 7, pp. 2558-2565.
Miyake, Kensuke, et al; A VCAM-like Adhesion Modecule on Murine Bone Marrow Stromal Cells Mediates Binding of Lymphocyte Precursors in Culture; The Journal of Cell Biology, vol. 114, No. 3, 668-565; Aug. 1991.
Li, Wenzhe, et al; Reduced a4B1 integrin/VCAM-1 interatctions lead to impaired pre-B cell repopulation tin alpha 1,6-fucosyltransferase deficient mice; Glycobiology, vol. 18, No. 1; 114-124; 2008.
Miyake, Kensuke, et al; Evidence for a Role in the Integrin VLA-4 in Lympho-hemopoiesis; J. Exp. Med, vol. 173, 599-607; Mar. 1991.
Ulyanova, Tatiana, et al., VACM-1 expressions in adult hemotopoietic and nonhematopoietic cells is controlled by tissue-inductive signals and reflects their developmental origin; Blood Journal; vol. 106, No. 1; Jul. 1, 2005.
Hechler, Beatrice, et al; Reduced Atherosclerotic Lesions in P2Y1/Apolipoprotein E Double-Knockout Mice, The Contribution of Non-Hematopoietic-Derived P2Y1 Receptors; Circulation AHA Journals; 2008.
Glanville; Stephanie H., et al.; Transplatation of Embryonic Spleen Tissue Reveals a Role for Adult Non-Lymphoid Cells in Initiating lymphoid Tissues Organization; Eur. J. Immunol. 2009; 39: 280-289.
Song, Jian; et al; Extracellular Matix of Secondary Lymphoid Organs Impacts at B-Cell Fate and Survival; Proc. Natl Acad. Sci; 10.1073 published online Jul. 11, 2013; E2915-E2924.
Ambardekar Vishakha V., et al; The Modification of siRNA with 3' Cholesterol to Increase Nuclease Protection and Suppression of Native mRNA by Select siRNA Polyplexes; NIH Public Access; Biomaterials; Feb. 2011; 32(5): 1404-1411.
Banerjee, Ena Ray; et al. Defining the molecular role of gp1phox in the immune manifestation of acute allergic asthma using a preclinical murine model; Clinical and Molecular Allergy; 2012, 10:2, 1-14.
Andrew Jefferson; Molecular Imaging with Optical Coherence Tomography Using Ligand-Conjugated Microparticles that Detect Activated Endothelial Cells: Rational Design through Target Quantification; Elesvier, Atheroclerosis 219; (2011) 579-587.
European Patent Office; Summons to Attend Oral Proceedings Pursuant to Rule 115(1) EPC; Application 13719147.1-1413/2841455; Aug. 3, 2017.

\* cited by examiner

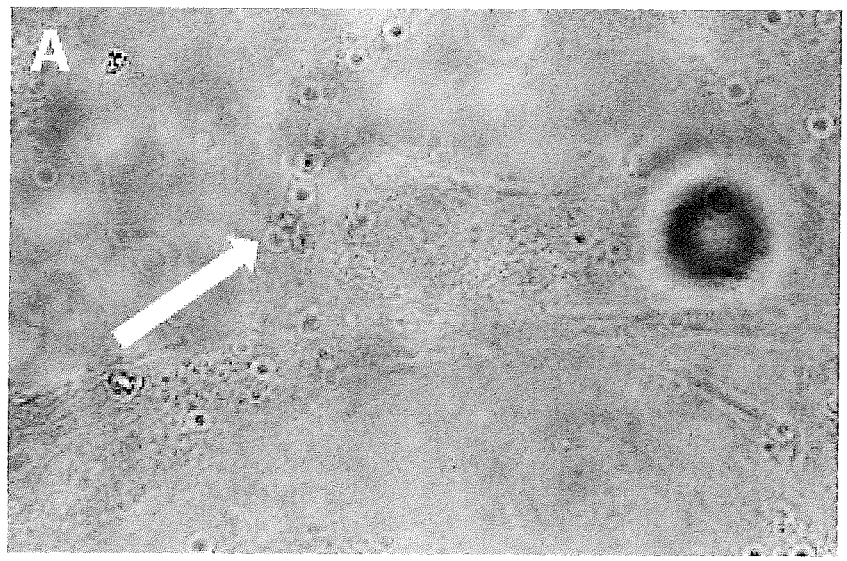

ANTIBODIES AGAINST CD106 (VCAM-1)

CROSS REFERENCE TO RELATED APPLICATIONS

This application is a national phase application under 35 U.S.C. § 371 that claims priority to PCT Application No. PCT/GB2013/051037 filed Apr. 24, 2013, which claims the benefit of Great Britain Application No. 1207155.1 filed Apr. 24, 2012, both of which applications are incorporated by reference herein in their entirety.

FIELD OF THE INVENTION

The present invention relates to antibodies that specifically bind to human VCAM-1, and in particular to the extracellular domain of VCAM-1 in the native state.

BACKGROUND TO THE INVENTION

Endothelial vascular cell adhesion molecule-1 (VCAM-1) and its ligand, $\alpha_4\beta_1$ integrin, are key mediators of leukocyte recruitment. These molecules play a role in the development of multiple sclerosis which is associated with leucocyte recruitment and subsequent inflammation, demyelination and axonal loss in the central nervous system. VCAM-1 and its ligand, $\alpha_4\beta_1$ integrin, are important mediators of mononuclear leucocyte recruitment and lesion initiation. VCAM-1 is not constitutively expressed on cerebral vascular endothelium, but is upregulated with endothelial activation. Selective blockade of this interaction in experimental autoimmune encephalitis results in abolition of both lymphocyte recruitment and the paralysis that usually follows.

There is also a close association of tumour colonies with the existing cerebral vasculature in both murine models of brain metastasis and human brain tissue containing metastases. Activation of the vascular endothelium is likely to occur during metastasis development. There is also evidence to suggest that tumour cells use inducible CAMs to promote their adhesion to the vascular endothelium. VCAM-1 has been found to be upregulated in lung and liver metastasis.

Antibodies to human VCAM-1 may be useful in the diagnosis and treatment of diseases and disorders associated with upregulation of VCAM-1 expression, such as multiple sclerosis and tumour metastasis. Currently available antibodies are not suitable for this purpose, and improved antibodies are required.

SUMMARY OF THE INVENTION

The present inventors have produced antibodies which are suitable for use in diagnosis. The antibodies of the present invention are directed to the extracellular domain of human VCAM-1. The antibodies of the present invention retain the ability to bind to human VCAM-1 in its native state, that is, when expressed on endothelial cells.

In accordance with the first aspect of the present invention, there is provided an antibody or fragment thereof that specifically binds to human endothelial vascular cell adhesion molecule-1 (VCAM-1), wherein the antibody or fragment thereof binds to the extracellular domain of VCAM-1, and wherein the antibody or fragment thereof binds to VCAM-1 when expressed on endothelial cells, wherein the antibody or fragment thereof is a human or humanized antibody, or fragment thereof.

In preferred embodiments of the present invention, the antibody is a monoclonal antibody.

Typically, the antibody has at least one CDR selected from SEQ ID NOs: 5, 6, 7, 11, 12 and 13, and may comprise the CDRs of 5, 6 and 7 and/or the CDRs of SEQ ID NOs: 11, 12 and 13.

In one embodiment of the present invention, the antibody or fragment thereof comprises:
(a) a light chain of SEQ ID NO: 3 or a light chain variable region amino acid sequence of SEQ ID NO: 4;
(b) a fragment of at least 7 amino acids of (a) which retains the ability to specifically bind to VCAM-1; or
(c) a variant of (a) having at least 70% identity amino acid sequence identity to a sequence of (a) and retaining the ability to specifically bind to VCAM-1.

The antibodies and fragments thereof can be used in methods of diagnosis. For diagnosis, the antibodies or fragments thereof may be conjugated to an ion oxide microparticle and used in the diagnosis of inflammatory disease in the central nervous system such as multiple sclerosis. The antibodies are particularly suitable for in vivo diagnosis.

The antibodies are also useful in the diagnosis of tumour metastasis.

BRIEF DESCRIPTION OF THE FIGURES

FIG. 1: TNF-stimulated HUVEC showing binding of beads with humanised anti-VCAM antibodies of the invention bound thereto around the membrane (arrows) in brightfield micrograph.

BRIEF DESCRIPTION OF THE SEQUENCE LISTING

SEQ ID NO: 1 is the extracellular domain of human VCAM-1.
SEQ ID NO: 2 is the nucleotide sequence of the light chain of the antibody.
SEQ ID NO: 3 is the light chain of the antibody.
SEQ ID NO: 4 is the variable region of the light chain of the antibody.
SEQ ID NOs: 5, 6 and 7 are CDRs 1, 2 and 3 respectively of the light chain of the antibody.
SEQ ID NO: 8 is the nucleotide sequence of the heavy chain of the antibody.
SEQ ID NO: 9 is the heavy chain of the antibody.
SEQ ID NO: 10 is the variable region of the heavy chain of the antibody.
SEQ ID NOs: 11, 12 and 13 are CDRs 1, 2 and 3 respectively of the heavy chain of the antibody.

DETAILED DESCRIPTION OF THE INVENTION

The present invention relates to antibodies that bind to VCAM-1. The antibodies preferably specifically bind to VCAM-1, that is they bind to VCAM-1 but they do not bind, or bind at a lower affinity, to other molecules. The antibodies in accordance with the present invention bind to the extracellular domain of human VCAM-1, and retain the ability to bind to human VCAM-1 in its native state, for example when expressed on endothelial cells. The invention also relates to uses for such antibodies, such as diagnostic uses.

The term VCAM-1 as used herein refers to human VCAM-1. The extracellular domain of human VCAM-1 has the sequence set out in SEQ ID NO: 1. The antibody in accordance with the present invention has the ability to bind to the extracellular domain of human VCAM-1. An antibody in accordance with the present invention can be generated using an isolated extracellular domain, for example of SEQ ID NO: 1.

An antibody of the invention has the ability to bind to VCAM-1 in its native state and in particular to VCAM-1 as expressed on the surface of human endothelial cells. Preferably, an antibody of the invention will bind specifically to VCAM-1. That is, an antibody of the invention will preferably bind to VCAM-1 with greater binding affinity than that at which it binds to another molecule. An antibody of the present invention binds to human VCAM-1. Such an antibody may have some binding affinity for VCAM-1 from other mammals, for example to primate VCAM-1.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

An antibody of the invention is preferably capable of binding to its target with an affinity that is at least two-fold, 10-fold, 50-fold, 100-fold or greater than its affinity for binding to another non-target molecule.

The antibodies described herein have affinities of $1.47 \times 10^{-7}$M, $3.28 \times 10^{-7}$M and 2.6 µM Kd. Low affinity antibodies are useful in accordance with the present invention given the potential high density of the target antigen. Also, the antibodies in accordance with the present application preferably have a low affinity in view of the use of the antibodies in a multivalent setting, for example, as a contrast agent bound to microparticles. Typically, antibodies according to the present invention have an affinity between 0.5 and 200 µM Kd, typically, between 1 and 50 µM Kd, such as between 1 to 10 µM Kd, or between $0.1 \times 10^{-7}$M to $100 \times 10^{-7}$M or between $0.1 \times 10^{-7}$M to $10 \times 10^{-7}$M or between $1 \times 10^{-7}$M to $10 \times 10^{-7}$M.

In accordance with the present invention, the antibodies of the present invention are preferably non-neutralising, such that the antibody does not interfere with the activity of VCAM-1. Such antibodies are useful in the diagnostic context, in particular where such antibodies are being used in vivo for targeting of contrast agents in order to avoid interference with the normal signaling/binding biological effects of VCAM-1. The ability of the antibody to neutralise VCAM can be determined using a competitive ELISA to identify if any dose-dependent reduction in the binding of VCAM-1 to its ligand VLA-4 occurs in the presence of the antibody. If no significant dose-dependent reduction to binding is observed, then the antibody is characterized as non-neutralising.

The antibodies of the invention can also be characterized by their on/off rates. Antibodies can be selected to have an on/off rate. A slower off rate of the antibodies is preferred so that the antibody binds to the target for a longer period of time to provide an increased imaging window. The antibodies of the present invention have been demonstrated to have Kon of 7400 $Ms^{-1}$ and a Koff of $1.1 \times 10^{-3} s^{-1}$. Preferred on and off rates are preferably +/−50%, more preferably +/−20%, more preferably +/−10% of these on/off rates.

An antibody of the invention typically binds to the same eptiope as the antibody having the sequence of SEQ ID NOs: 3 and 9. As used herein, the term "epitope" generally refers to the site on a target antigen which is recognised by an immune receptor such as an antibody. Preferably it is a short peptide derived from or as part of a protein. However the term is also intended to include peptides with glycopeptides and carbohydrate epitopes. A single antigenic molecule, such as a target protein as described herein, may comprise several different epitopes. Epitopes can be identified from knowledge of the amino acid and corresponding DNA sequences of the peptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81.

The location of an epitope may be identified by routine methods. For example, the general location of an epitope may be determined by assessing the ability of an antibody to bind to different fragments or variant VCAM-1 polypeptides. The specific amino acids within VCAM-1 that make contact with an antibody may also be determined using routine methods, such as that described in the Examples. For example, the antibody and target molecule may be combined and the antibody/target complex may be crystallised. The crystal structure of the complex may be determined and used to identify specific sites of interaction between the antibody and its target.

An antibody of the invention may bind to the same epitope or region as another antibody of the invention. For example, where an antibody of the invention is known, other antibodies of the invention may be identified by comparing their binding to VCAM-1 with that of the known antibody.

In one embodiment, an antibody of the invention may bind to the same epitope or region as the antibodies described herein having SEQ ID NOs: 3 and 9. An antibody of the invention may be an antibody that binds to the same epitope in VCAM-1 as the antibodies described herein having SEQ ID NOs: 3 and 9. The antibody of the invention may comprise a heavy chain and/or a light chain.

An antibody of the invention may have the ability to cross-compete with another antibody of the invention for binding to VCAM-1 or another appropriate target as described herein. For example, an antibody of the invention may cross-compete with one or more of the antibodies described herein, and in particular an antibody having SEQ ID NOs: 3 and 9 for binding to VCAM-1 or to a suitable fragment or variant of VCAM-1 that is bound by the antibodies. Such cross-competing antibodies can be identified based on their ability to cross-compete with a known antibody of the invention in standard binding assays. For example, BIAcore analysis, ELISA assays or flow cytometry may be used to demonstrate cross-competition. Such cross-competition may suggest that the two antibodies bind to the same or similar epitopes.

An antibody of the invention may therefore be identified by a method that comprises a binding assay which assesses whether or not a test antibody is able to cross-compete with a known antibody of the invention for a binding site on the target molecule. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the VCAM-1 protein as the known antibody of the invention. A test antibody that is identified as cross-competing with a known antibody of the invention in such a method is also a potential antibody according to the present invention. The fact that the test antibody can bind VCAM-1 in the same region as a known antibody of the invention and cross-compete with the known antibody of the invention suggests that the test antibody may act as a ligand at the same binding site as the known antibody and that the test antibody may therefore mimic the action of the known antibody.

The known antibody of the invention may be an antibody as described herein, such as one of the VCAM-1 antibodies as described herein or any variant or fragment thereof as described herein that retains the ability to bind to VCAM-1. An antibody of the invention may bind to the same epitope as one or more of the antibodies of SEQ ID NOs: 3 and 9 as described herein or any variant or fragment thereof as described herein that retains the ability to bind to VCAM-1.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. Preferably the other molecule is not identical to the target molecule. Preferably the target molecule is not a fragment of the target molecule.

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. An antibody of the invention may be a chimeric antibody, a CDR-grafted antibody, a human or humanised antibody or an antigen binding portion of any thereof. For the production of both monoclonal and polyclonal antibodies, the experimental animal is suitably a mammal such as a goat, rabbit, rat or mouse.

Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation of a suitable animal, with the antigen of interest. Blood may be subsequently removed from the animal and the Ig fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas producing monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be replated, screened again, and if still positive for suitable IgG, the monoclonal antibodies can be subcloned at least twice by limiting dilution. The stable subclones can then be cultured in vitro to generate small amounts of antibody in tissue culture medium for characterization.

The term "antigen-binding portion" of an antibody refers to one or more fragments of an antibody that retain the ability to specifically bind to an antigen, such as VCAM-1 or another target protein as described herein. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The antibodies of the present invention may be modified or selected to have low immunogenicity and/or low T-cell activation or reduced immunogenicity and/or T-cell activation compared to an antibody that has not been so selected or modified.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds VCAM-1 or a particular part, e.g. epitope, of VCAM-1, the specificity of the antibody may be assessed by determining whether or not the antibody also binds to other molecules or modified forms of VCAM-1 that lack the part of interest.

Once a suitable antibody has been identified and selected, the amino acid sequence of the antibody may be identified by methods known in the art. The genes encoding the antibody can be cloned using degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

The present inventors have identified antibodies as described in the examples. The present invention encompasses these antibodies and variants and fragments thereof which retain one or more activities of these antibodies. The activities of these antibodies include the ability to bind the extracellular domain of VCAM-1, and the ability to bind to human VCAM-1 when expressed on endothelial cells.

A suitable fragment or variant of this antibody will retain the ability to bind to VCAM-1. It will preferably retain the ability to specifically bind to VCAM-1. It will preferably retain the ability to specifically bind to the same epitope or region of the VCAM-1 molecule as the antibody, such as an antibody having SEQ ID NOs: 3 and 9 from which it is derived. It will also retain one or more additional functions of the antibody from which it is derived, such as the ability to bind to human VCAM-1 when expressed on endothelial cells.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the antibodies or a variant thereof. The antibody of the invention may be or may comprise an antigen binding portion of these antibodies or a variant thereof as discussed further above. For example, the antibody of the invention may be a Fab fragment of one of these antibodies or a variant thereof or may be a single chain antibody derived from one of these antibodies or a variant thereof.

The amino acid sequences of the variable regions of the light and heavy chains of the antibody are given in SEQ ID NOs: 4 and 10 respectively. The CDRs for the VL chain are shown in SEQ ID NOs: 5, 6 and 7. The CDRs for the VH chain are shown in SEQ ID NOs: 11, 12 and 13.

An antibody of the invention may comprise a light chain amino acid sequence comprising the sequence shown in SEQ ID NO: 3 or a fragment or variant thereof. An antibody may additionally or alternatively comprise a heavy chain amino acid sequence comprising the sequence shown in SEQ ID NO: 9 or a fragment or variant thereof as described herein.

An antibody of the invention may comprise the VL amino acid sequence of SEQ ID NO: 4, or a fragment or variant thereof. An antibody of the invention may comprise the VH amino acid sequence of SEQ ID NO: 10, or a fragment or variant thereof. An antibody of the invention may comprise both (a) the VL amino acid sequence of SEQ ID NO: 4, or a fragment or variant thereof and (b) the VH amino acid sequence of SEQ ID NO: 10, or a fragment or variant thereof.

An antibody of the invention may comprise a fragment of one of the VL or VH amino acid sequences shown in SEQ ID NOs: 4 and 10. For example, an antibody of the invention may comprise a fragment of at least 7, at least 8, at least 9, at least 10, at least 12, at least 15, at least 18, at least 20 or at least 25 consecutive amino acids from SEQ ID NO: 4 or 10. Such a fragment will preferably retain one or more of the functions discussed above, such as the ability to bind to VCAM-1.

An antibody of the invention may comprise a CDR region from the specific antibody identified herein such as a CDR region from within SEQ ID NO: 3 or 9. Such an antibody will preferably retain the ability to bind to VCAM-1 as described herein. For example, the CDR sequences within the light chain of SEQ ID NO: 3 are shown in SEQ ID NOs: 5, 6 and 7. The CDR sequences within the heavy chain of SEQ ID NO: 9 are shown in SEQ ID NOs: 11, 12 and 13. An antibody of the invention may comprise one or more of the CDR sequences shown in SEQ ID NOs: 5 to 7 and 11 to 13. For example, an antibody of the invention may comprise one, two or all three of the amino acid sequences of SEQ ID NOs: 5, 6 and 7. An antibody of the invention may alternatively or additionally comprise one, two or all three of the amino acid sequences of SEQ ID NOs: 11, 12 and 13. Antibody of the invention may comprise all six amino acid sequences of SEQ ID NOs: 5 to 7 and 11 to 13.

An antibody of the invention may alternatively be or may comprise a variant of one of these specific sequences. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies according to the invention have an amino acid sequence which has more than 60%, or more than 70%, e.g. 75 or 80%, preferably more than 85%, e.g. more than 90 or 95% amino acid identity to SEQ ID NO: 3, 4, 9 or 10, or a fragment thereof. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10.

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

The present invention thus provides antibodies having specific VH and VL amino acid sequences and variants and fragments thereof which maintain the function or activity of these VH and VL domains.

Accordingly, an antibody of the invention may comprise:
  (a) a light chain of SEQ ID NO: 3 or a light chain variable region amino acid sequence of SEQ ID NO: 4;
  (b) a fragment of at least 7 amino acids of (a) which retains the ability to specifically bind to VCAM-1; or
  (c) a variant of (a) having at least 70% amino acid sequence identity to a sequence of (a) and retaining the ability to specifically bind to VCAM-1.

An antibody of the invention may comprise:

(a) a heavy chain of SEQ ID NO: 9 or a heavy chain variable region amino acid sequence of SEQ ID NO: 10;

(b) a fragment of at least 7 amino acids of (a) which retains the ability to specifically bind to VCAM-1; or (c) a variant of (a) having at least 70% amino acid sequence identity to a sequence of (a) and retaining the ability to specifically bind to VCAM-1.

An antibody of the invention may comprise the light chain variable region of SEQ ID NO: 4 and the heavy chain variable region of SEQ ID NO: 10.

An antibody of the invention may comprise:

(a) the light chain of SEQ ID NO: 3 or the light chain variable region of SEQ ID NO: 4 and the heavy chain of SEQ ID NO: 9 or the heavy chain variable region of SEQ ID NO: 10;

(b) a variant of (a) in which one or both of the heavy chain and light chain sequences is modified such that it comprises a fragment of at least 7 amino acids of the sequence specified in (a); or (c) a variant of (a) or (b) in which one or both of the heavy and light chain sequences is modified such that it has at least 70% amino acid sequence identity to a sequence of (a) or (b);

wherein the antibody retains the ability to specifically bind to VCAM-1.

As explained above, an antibody of the invention may bind to the same epitope or region as another antibody of the invention. Thus it will be seen that such an antibody may bind to the same epitope or region of VCAM-1 as any of the specific antibodies, fragments and variants described herein.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of SEQ ID NO: 3 or 9, or a variant or fragment thereof as described above. Such a polynucleotide may consist of or comprise a nucleic acid sequence of any one of SEQ ID NOs: 2 and 8. A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of SEQ ID NOs: 2 and 8 preferably at least 80 or 90% and more preferably at least 95%, 97% or 99% homologous thereto. Preferably homology and identity at these levels is present at least with respect to the coding regions of the polynucleotides of SEQ ID NOs: 2 and 8. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et at (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et at (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence of SEQ ID NOs: 2 and 8 or may be derived from a variant polynucleotide as described herein. Preferably such fragments are between 30 and 300 residues in length, e.g. 30 to 300, 30 to 200, 30 to 100, 100 to 200 or 200 to 300 residues. Alternatively, fragments of the invention may be longer sequences, for example comprising at least 50%, at least 60%, at least 70%, at least 80% or at least 90% of a full length polynucleotide of the invention.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et at (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293T, CHO, HeLa, NS0 and COS cells. Preferably the cell line selected will be one which is not only stable, but also allows for mature glycosylation and cell surface expression of a polypeptide.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition comprising one or more molecules of the invention, such as one or more antibodies of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the antibody may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Also within the scope of the present invention are kits comprising antibodies or other compositions of the invention and instructions for use. The kit may further contain one ore more additional reagents, such as an additional therapeutic or prophylactic agent as discussed above.

The antibodies in accordance with the present invention maybe used in diagnosis, in particular in humans. The antibodies can be used in vivo as diagnostic agents, to detect increased VCAM-1 expression on endothelial cells, to identify and quantify expression of VCAM-1, for example, for use in methods of imaging inflammation. The antibodies of the present invention are particularly useful in detection of acute brain inflammation by magnetic resonance imaging. Such detection methods can be used to accelerate diagnosis, quantify disease activity and to guide therapy. Detection of VCAM-1 on an acute brain inflammation can be used in the diagnosis of multiple sclerosis, and is particularly useful at a time when pathology is otherwise undetectable.

For magnetic resonance imaging, the antibodies of the present invention are typically conjugated to microparticles, and in particular iron oxide containing microparticles. Microparticles of iron oxide are known and described in the prior art. Antibodies in accordance with the invention can be conjugated to such particles using any suitable methods. In preferred embodiments of the invention, the antibodies are conjugated to iron containing colloidal particles, or multimeric particles as described in more detail below.

The iron containing colloidal particle according to the present invention may be any suitable iron containing particle. Suitable particles include those comprising iron hydroxide, iron oxide hydrate, iron (II) oxide, iron (III) oxide, mixed iron oxide, metallic iron or mixtures thereof. In mixed iron oxides other metal oxides such as oxides of cobalt, nickel, manganese, beryllium, magnesium, calcium, barium, strontium, copper, zinc, platinum, aluminium, chromium, bismuth, rare earth metals and mixtures thereof can be present. In preferred embodiments, the iron containing particle is an iron (II) or iron (III) oxide or an iron hydroxide or a mixture thereof. In a particularly preferred embodiment, the particle is iron oxide, in particular iron (III) oxide. The particles are preferably less than 1 mm in size, preferably less than 100 nm in size, and are typically less than 80 nm, preferably less than about 50 nm and may be as small as 5 nm.

The particles preferably are cross-linked iron oxide particles (CLIOs). Such particles are described for example in Wunderbaldinger et al, Acad Radiol 2002 9 (supple 2) S304-S306. These particles comprise a core of iron oxide, that is preferably 3 to 10 nm, preferably 3 to 5 nm in size, and a dextran coat. Preferably the dextran coat is formed by crosslinking the dextran to form a dextran chain around the iron oxide core. Typically such particles may be produced by reacted dextran coated iron oxide particles in presence of epichlorohydrin and ammonia.

Such particles can be derivatised, for example with amine containing groups for conjugation to the targeting moieties according to the present invention. For example, amino groups of a dextran-coated iron oxide particle can react with a 2-cyanomethyl-containing compound to produce functionalised iron oxide particles.

The antibodies in accordance with the present invention can also be conjugated to multimeric metal containing particles, such as those described in WO2008/035069. The metal-containing particles in the multimeric particle are generally from 1 nm to 200 nm in diameter, preferably from 1 to 100 nm, more preferably from 5 to 20 nm. Clearly when these particles are manufactured there is a spread of particle diameters, therefore the range above refers to the average particle diameter. The average particle diameter can be determined as a root mean squared diameter, e.g. as measured by laser scattering. Usually a Brownian distribution of particle sizes will be obtained, of which the peak is considered the average particle diameter.

The resulting multimeric particles are generally from 200 nm to 2 μm in diameter, more preferably from 500 nm to 1.5 μm in diameter, for example around 1 μm. As with the metal-containing particles, there will be a spread of diameters for the multimeric particles, with the ranges above referring to the average diameter. One multimeric particle will generally comprise around one million of the metal-containing particles; more preferably one multimeric particle will consist of around one million of the metal-containing particles.

In one embodiment, in order to obtain multimeric particles within a preferred size range, the metal-containing particles and linker groups can be reacted in quantities and under conditions such that much larger multimeric particles or aggregate particles are first obtained. These over-sized particles can then be physically broken down into multimeric particles of the correct size, for example by milling or pulverising (e.g. by mechanical sheer forces).

The metal-containing particles which form the multimeric particles may be the same or different. For example, the multimeric particles may comprise a number of different metal-containing particles (containing different metals and/or different coatings). Alternatively, the multimeric particles may comprise a single type of metal-containing particle, such that all metal-containing particles comprise the same metal and the same coating.

The metal-containing particles contain a central metal or metal oxide core. The metal or metal oxide core is at least partially covered with a coating which is covalently bonded to one or more linker groups. Preferably the metal or metal oxide core is completely covered by said coating. In order for the covalent bond to be formed, then prior to formation of the multimeric particle the coating must be functionalised in order to covalently bond to the linker groups.

Suitable cores include iron-containing colloidal particles. For example, suitable cores include those comprising iron hydroxide, iron oxide hydrate, iron (II) oxide, iron (III) oxide, mixed iron oxide, metallic iron or mixtures thereof. In mixed iron oxides other metal oxides such as oxides of cobalt, nickel, manganese, beryllium, magnesium, calcium, barium, strontium, copper, zinc, platinum, aluminium, chromium, bismuth, rare earth metals and mixtures thereof can be present. Preferably the core comprises an iron (II) or iron (III) oxide or an iron hydroxide or a mixture thereof. More preferably the core comprises iron oxide, in particular iron (III) oxide.

For applications where for example a luminescent property is required (e.g. luminescent probes, suitable particles include gold nanoparticles and cadmium sulphide particles (cadmium sulphide quantum dots).

The coatings include well-known materials which have been used in the past to coat metal particles such as SPIOs and CLIOs. Suitable materials include long-chain sugars and the like, for example dextran, carbodextran, mannan, cellulose and starch-based polymers. It is also possible to use materials such as dendrimers. Preferably the coating comprises dextran, more preferably the coating consists of dextran. Where possible, the coatings may comprise materials which are cross-linkable. However, it is preferred that the coating is not cross-linked.

The coatings either provide or can be pre-reacted in order to provide functionalisation capable of bonding to the linker groups. For example, a dextran coating can provide amine groups which are capable of being reacted with a linker group in a process for preparing the multimeric particles. Alternatively, a coating can be pre-reacted, prior to reaction with a linker group, to form a functional group which is capable of reacting with a linker group in a process for preparing the multimeric particles.

Prior to formation of the multimeric particles, each metal-containing particle, comprising a metal or metal oxide core covered with a coating as described above, contains at least one functional group capable of reacting with a linker group. Preferably each metal-containing particle will contain a number of such functional groups, allowing bonds to be formed with a number of linker groups.

The linker groups in the multimeric particles act both to bind the metal-containing particles together and to maintain distance between said metal-containing particles. The length of the linker group can thus be manipulated in order to achieve optimal separation of the multimeric particles.

At least a portion of the linker groups are cleavable, thus allowing the multimeric particles to be broken down into smaller particles. Depending on the structure of the multimeric particle, a different number of linker groups will need to be cleaved in order to cause breakdown of the multimeric particle. For example, if two clusters of metal-containing particles (each cluster comprising metal-containing particles covalently bonded by linker groups) are bonded to each other by a single linker groups, then only this single linker group will need to be cleaved in order to cause degradation of the multimeric particle. Thus, in a preferred embodiment, the portion of said linker groups which are cleavable is chosen such that it is sufficient to cause degradation of the multimeric particle. As used herein, degradation means breakdown of the multimeric particle into two or more constituent parts, these constituent parts being separate from one another, not being covalently bonded to one another).

More preferably the majority of the linker groups are cleavable, most preferably all of the linker groups are cleavable, thus allowing for the multimeric particles to be broken down into their constituent metal-containing particles. However, clearly the types of linker groups and their relative proportions can be chosen in order to manipulate both the length of time before degradation, and also the level of degradation which occurs. For example a portion of the linker groups could be chosen to be cleavable under certain conditions in vivo, with the remaining linker groups being chosen to be either non-cleavable in vivo, or cleavable under different conditions or on a much longer timescale. Thus, the degradation of the multimeric particles can be tuned according to the purpose for which the multimeric particles are to be used.

Preferably the linker groups are stable in a carrier substance in which the multimeric particles can be stored, but at least some are cleavable after administration into a sample. For example, the linker groups may be cleavable enzymatically, or cleavable by another mechanism in vivo allowing breakdown of the multimeric particles following administration to the human or animal body.

Preferably the linker groups comprise at least one such cleavable group. Particularly preferred cleavable groups include peptide bonds and ester linkages, as well as mixed acetal linkages, particularly between rings of a di- or higher polysaccharide. Other suitable cleavable groups include those known to a person skilled in the art, for example ether linkages. Thus, preferred cleavable groups include groups of formula —NR—CO— where R is an amino acid residue, and —CO—O— groups, as well as acetal groups. Examples of linker groups that are particularly useful in the present invention include linker groups containing proteins, peptides, polysaccharides and other carbohydrates, ester, amide, acetal, ether and phosphate linkages, for example DNA. Furthermore, each linker group can comprise more than one cleavable group. If more than one cleavable group is present, the groups may be the same or different.

Preferably the cleavable group is enzymatically cleavable. Enzymatic cleaving has particular relevance where the linker group comprises a peptide sequence. The exact nature of the peptide sequence can be manipulated in order to manipulate the ease and specificity of degradation. Enzymatic cleaving also allows multimeric particles having a particular peptide-containing linker group to remain intact during progress through a patient until it reaches a part of the body where the relevant enzyme is found. Accordingly, choice of linker group can be used to control the region of the body in which cleaving occurs and, therefore, at which breakdown of the multimeric particle occurs.

Accordingly, in one embodiment, the cleavable group is a group which is cleavable by the enzyme thrombin. Thus, the linker groups may comprise at least one group which is cleavable by thrombin. Typically, the group which is cleavable by thrombin is a peptide which comprises the known thrombin cleavage sequence Phe-Val-Arg. Typically, the peptide further comprises amino acid spacer units, for instance glycine spacer units, either side of the cleavage sequence Phe-Val-Arg.

In the case of fibronectin and collagen linking groups, as an example, these are useful in imaging of regions where collagenase activity is present, for example in sites of active inflammation. At such sites degradation of the large to small particles gives rise to improved local contrast.

In addition to the functionalisation which is present in, or is introduced into, the coatings and which allows binding to the linker groups, the metal-containing particles are further functionalised in order to provide targeting moieties.

For example an antibody in accordance with the present invention can be covalently linked to a dextran coating of a metal-containing particle using a periodate-oxidation/borohydride-reduction method, which, through the formation of Schiff bases as intermediates, covalently links the amine (lysine) groups of a monoclonal antibody to alcohol groups of the dextran coat. Such functionalisation of metal-containing particles is known in the art. Other methods are also known for attaching antibodies to the metal-containing particles, such as through glutaraldehyde crosslinking, complexing through ultrasonication, using biotin streptavidin system and amine-sulfhydryl group linkage.

In addition to the targeting moieties, the metal-containing particles can be further functionalised to provide additional properties, for example to improve solubility, phagocytosis, non-antigenicity or to act as in vivo lifetime modulators.

As an example, the particles can be further functionalised with polyethylene glycol (PEG) moieties or similar solubilising groups in order to improve solubility. Thus, the particles can be PEGylated. Other exemplary functionalising groups will be known to the skilled person.

The conjugates according to the present invention can be used as contrast agents in methods of imaging. The agents of the present invention are particularly useful as contrast agents using magnetic resonance imaging (MRI). The agents can be delivered to the patient under investigation by any suitable route, but are typically provided by injection, usually intravenous injection. The agents of the present invention may cross the blood brain barrier and so may be particularly useful in the monitoring or diagnosis of conditions affecting the brain. In a preferred embodiment, the contrast agents are used in the monitoring and diagnosis of inflammation.

In a particularly preferred embodiment according to the present invention, the agents are used in the monitoring and diagnosis of inflammation in the brain, and are particularly useful in the diagnosis of multiple sclerosis, and brain metastases. The agents of the present invention have the advantage of crossing the blood brain barrier and so may be used to provide an indication of inflammation and other disorders in the brain before the condition is advanced.

The antibodies in accordance with the present invention can also be used more generally in the detection of inflammation, and also in the detection and diagnosis of tumour metastasis. In particular, VCAM-1 has been found to be upregulated in a variety of metastases including metastases to the lung, liver and brain. The antibodies in accordance with the present invention can thus be used in the early diagnosis and detection of metastasis. For detection of metastasis to the brain, typically, the metal-containing particles discussed above are used.

The present invention is further illustrated by the following examples which should not be construed as further limiting. The contents of all figures and all references, patents and published patent applications cited throughout this application are expressly incorporated herein by reference.

EXAMPLES

Production of Mouse Monoclonal Against Human VCAM

A rat anti-mouse VCAM antibody was initially used in rodent laboratory imaging studies. This antibody is commercially available antibody from Southern Biotech and was raised in rat against mouse VCAM. The goal was to make an antibody against HUMAN VCAM, displaying properties required for MRI studies. The extracellular domain of recombinant Human VCAM was used to make MOUSE hybridoma lines expressing antibodies which cross-reacted with recombinant human VCAM by a rapid screen dot blot. Results from this assay identified 11 clones for further analysis.

Assays Carried to Select the Mouse Monoclonal Antibody to go Forward to Humanisation The studies detailed in table 1 demonstrate the assays which were carried out to assess which of the 11 hybridoma clones were suitable to move forward into the humanisation process.

TABLE 1

Studies used in assessing ideal antibody for humanisation

| Assay | Purpose |
| --- | --- |
| Immunohistochemistry on humanvascular endothelial cells (Study 1) | To assess recognition of VCAM-1 by HuVCAM in a system where known quantities of the protein are elevated following a 4 h exposure to TNF. |
| Competition immunohistochemistry (Study 2) | To demonstrate the specificity of antibody binding to target VCAM by preincubation with recombinant VCAM. Result: target was VCAM. |
| Immunohistochemistry on human brain biopsies (Study 3) | To assess the selectivity of HuVCAM to bind to tumourous and pre-tumorous areas in known brain metastasis patients. Result: antibody binds to cancerous areas, but not normal areas. |
| Immunohistochemistry on human brain biopsies (Study 4) | To compare HuVCAM pattern of immunoreactivity versus a commercial antibody which recognizes human VCAM. Result: An identical spatial distribution was observed between out antibody and commercially available antibodies. |
| Immunohistochemistry on inflamed rodent and primate tissue (Study 5) | To assess cross reactivity of HuVCAM in inflamed tissue from different species. Result: the antibody selected recognises mouse, rat and primate in addition to the target human VCAM. |
| Biacore analysis (Study 6) | To assess binding affinity and Kon/Koff rates of hybridomas in comparison to the commercial rodent antibody used in laboratory studies. Result: the antibody has a slower on rate and slower off rate than the commercial rat antibody which increases the imaging window. Antibody preferentially selected on this basis. |

Immunohistochemistry on Human Vascular Endothelial Cells (Study 1)

11 clones immunopositive for recombinant VCAM by dot blot were serotyped, 8 were IgG and 3 were IgM. IgM clones were not useful and were deselected. The 8 remaining clones were screened by using immunohistochemistry against human vascular endothelial cells with were either unstimulated or had been exposed to TNF for 4 h, a cytokine known to upregulate TNF. Our preferred antibody would show selective immunopositivity on the luminal side of the endothelial cells when stimulated with TNF, but no immunopositivity in the unstimulated state. The results demonstrated that while none of the antibodies displayed non-specific binding to unstimulated cells, only some of the antibodies displayed immunopositivity to stimulated cells. Thus all of the clones currently being tested showed positive immunoreactivity against the immunizing protein (extracellular domain of VCAM-1), but only selected antibodies were able to detect the VCAM-1 protein in its native state in an intact cell after stimulation with TNF. It was expected that all of the antibodies would detect the VCAM-1 protein in its native state, but it is clear that some components of the extracellular domain are more accessible to antibody binding than others. From this data, we selected the two antibodies which recognized VCAM at the lowest concentration. These antibodies were 1-1, 2-1, 7-1 and 11-1.

Competition Immunohistochemistry (Study 2)

Competition assays using recombinant human VCAM-1 on TNF stimulated and non-stimulated huVECs on coverslips.—To ensure specificity of binding to human VCAM-1, selected antibodies (1:1, 2:1, 7:1 and 11:1) where incubated with 2 µg/ml of recombinant human VCAM-1 or an irrelevant protein (rat recombinant IL-1R2) for 2 h at room temp followed by use of the antibodies in standard immunohistochemistry on naïve and TNF stimulated HUVECs. Result—The specific anti-human VCAM-1 immunopositivity is competed out by the increasing incubation concentrations of recombinant human VCAM-1 for all antibodies.

Immunohistochemistry on Human Brain Biopsies (Study 3)

We assessed HuVCAM for immunoreactivity to VCAM-1 in biopsies from human patients with brain metastasis. The antibodies (1:1, 2:1, 7:1 and 11:1) demonstrated immunopositivity in intra- and peri-tumoral endothelial cells, perivascular cells and macrophages. These results suggest that the antibodies should selectively bind to upregulated VCAM-1 on the vasculature of tumours and pre-tumourous tissue in humans. It is of note that in vivo, the antibody given intravenously will have access to only the endothelial VCAM-1 and not the parenchymal microglia and therefore should display a selective signature for imaging. The antibody binds to the blood side of the blood brain barrier. From the antibodies which displayed similar patterns of immunoreactivity (1:1, 2:1, 7:1 and 11:1), we selected 1-1 and 1-2 for further study as they bound at lower concentrations than the others.

Immunohistochemistry on Human Brain Biopsies (Study 4)

We have data to show that HuVCAM labels the human biopsies (Study 3) in a pattern indistinguishable from commercial anti-human VCAM-1 antibodies available.

Immunohistochemistry on Inflamed Rodent and Primate Tissue (Study 5)

We assessed 1-1 and 1-2 for cross reactivity to VCAM-1 in unilaterally injected interleukin-1 beta (IL-1 beta) mouse and rat brain and HIV-infected primate by immunohistochemistry. Results showed immunopositivity on endothelial cells in the ipsilateral hemisphere of the IL-1beta-inflamed mouse and rat. The unilateral nature of the binding was expected as the inflammogen is injected on one side only. No positive immunoreactivity was observed in naïve tissue. A similar finding was observed in the HIV-infected primate where the VCAM-activated vasculature was selectively positive. These results demonstrated that the antibodies have efficacious binding in rodents and primate.

Biacore Analysis (Study 6)

We carried out Biacore analysis on the antibodies (1-1 and 1-2) to assess binding efficacy. 1-1 had a higher binding efficacy and therefore the antibody was selected for further Biacore analysis and was chosen as our antibody to enter into the full humanisation process. In these experiments, we compared the binding properties of the chosen clone for humanisation 1-1 with those of the commercial rat antibody used in our rodent studies. Results show that the clone we have selected has a very similar binding affinity for its respective species.

Results showed that the latter form had an affinity for human VCAM-1 of 146 nM with a Kon of 7400 Ms−1 and a Koff of $1.1\times10^{-3}$ s−1, whereas the rodent VCAM-1 antibody had an affinity of 61 nM, a Kon of 33120 Ms−1 and a Koff of $2.0\times10^{-3}$ s−1. Thus, the rodent model antibody had an affinity 2-fold higher than HuVCAM, comprising an on rate that was 4 fold faster and an off rate that was 2 fold faster. The slower off-rate of HuVCAM is preferable since this means that it will remain bound to the target for longer giving an increased 'imaging window'. The slower on-rate can be compensated for by either increasing the binding time, or by increasing the concentration of the antibody. Due to the multivalent application for the antibody, there should be no concerns at this difference in affinity.

Humanisation Process

From the starting mouse monoclonal raised against the extracellular domain of human VCAM-1, we generated a chimeric antibody comprising mouse monocolonal antibody V regions and the human IgG4/kappa constant regions. The V regions were inserted into expression vectors and their affinity for human recombinant VCAM-1 assayed. We next developed a fully humanised antibody using Composite Human Antibody™ technology. The sequences of the starting monoclonal antibody heavy and light chain V regions were analysed to identify complementarity-determining regions, unusual amino acids and residues critical to binding. A series of humanised heavy and light chain V regions were designed entirely from human V region sequences incorporating these identified residues. Variant human sequence segments with significant incidence of potential T cell epitopes as determined by in silico methods (MHC class II binding prediction software (iTope™) and a database of peptides known to be either positive or negative for T cell activation (TCED™) were discarded, whilst those previously found to be negative for T cell activation were preferentially included. Sequence segments screened in this way were used to design humanised variants devoid of T cell epitopes for construction. Expression plasmids were constructed encoding fully humanized antibodies with human constant regions. The humanised antibodies were expressed transiently in HEK293 cells and purified antibodies were tested for binding to human VCAM-1 in a competition ELISA format (competing against a fixed concentration of biotinylated mouse antibody). The lead antibody was selected based upon binding activity to human VCAM-1. Stable NS0 cell lines have also been produced for the lead humanised antibody and these have been used to prepare larger quantities of purified antibody for conjugation to mMPIO. The lead antibody from HEK293 cells was selected based upon binding activity to human VCAM-1. See characterisation tests below.

Characterisation of the Humanised Antibody

The following assays were carried out in order to characterise the properties of our humanised VCAM antibody

| Assay | Purpose |
|---|---|
| Nucleotide and protein sequencing (Study 7) | To obtain the whole sequences of the humanised antibody. |
| T cell episcreen (Study 8) | Assess immunogenicity of antibody sequences in human plasma. We demonstrate low levels of immunogenicity in our antibody. |
| Competitive ELISA (Study 9) | To assess binding efficacy of the humanised antibody in comparison to the non-humanised version. |
| Immunohistochemistry on TNF stimulated and non-stimulated human vascular endothelial cells (Study 10) | To assess whether the humanised antibody could recognise human VCAM when induced in endothelial cells. |
| Binding to human isolated vessels (Study 11) | Flow binding assay ex vivo to demonstrate binding of HuVCAM-mMPIO to human VCAM-1 on isolated human vessels. |

Nucleotide and Protein Sequencing (Study 7)

The full protein and nucleotide sequences for the humanised antibody are shown in SEQ ID NOs: 2, 3, 8 and 9. The nucleotide sequences are genomic i.e. they contain the natural introns in our expression vectors.

The protein sequences of the heavy and light chains are set out below showing the position of the regions of the antibody.

```
IgG4(S241P)VH4 Full Protein Sequence
                                        (SEQ ID NO: 9)
QVTLKESGPALVKPTQTLTLTCSFSGFSLSTSGLGVSWIRQPSGK      50
ALEWL

AHVYWDDDKLYNPSLKSRLTISKDTSKNQVVLTMTNMDPVDTATY     100
YCGRR

AFYGNNGAYAMDYWGQGTLVTVSSASTKGPSVFPLAPCSRSTSES    150
TAALG

CLVKDYFPEPVTVSWNSGALTSGVHTFPAVLQSSGLYSLSSVVTV    200
PSSSL

GTKTYTCNVDHKPSNTKVDKRVESKYGPPCPPCPAPEFLGGPSVF    250
LFPPK

PKDTLMISRTPEVTCVVVDVSQEDPEVQFNWYVDGVEVHNAKTKP    300
REEQF

NSTYRVVSVLTVLHQDWLNGKEYKCKVSNKGLPSSIEKTISKAKG    350
QPREP

QVYTLPPSQEEMTKNQVSLTCLVKGFYPSDIAVEWESNGQPENNY    400
KTTPP

VLDSDGSFFLYSRLTVDKSRWQEGNVFSCSVMHEALHNHYTQKSL    450
SLSLG

K.                                                451

Variable region: residues 1 to 124
                                        (SEQ ID NO: 10)
QVTLKESGPALVKPTQTLTLTCSFSGESLSTSGLGVSWIRQPSGKALEWL
AHVYWDDDKLYNPSLKSRLTISKDTSKNQVVLTMTNMDPVDTATYYCGRR
AFYGNNGAYAMDYWGQGTLVTVSS CDR1: residues 31 to 37
                                        (SEQ ID NO: 11)
TSGLGVS
CDR2: residues 52 to 67
                                        (SEQ ID NO: 12)
HVYWDDDKLYNPSLKS CDR3: residues 100 to 113
                                        (SEQ ID NO: 13)
RAFYGNNGAYAMDY CH1: residues 125 to 222

Hinge: residues 223 to 234

CH2: residues 235 to 344

CH3: residues 345 to 451

VK3 Full Protein Sequence
                                        (SEQ ID NO: 3)
EIVMTQSPAILSLSPGERATLSCRASQSISDYLHWYQQKPGQAPR     50
LLIKY

ASQSISGIPARFSGSGSGSDFTLTISSLQPEDFAVYYCQNGHSFP    100
LTFGQ

GTKLEIKRTVAAPSVFIFPPSDEQLKSGTASVVCLLNNFYPREAK    150
VQWKV

DNALQSGNSQESVTEQDSKDSTYSLSSTLTLSKADYEKHKVYACE    200
VTHQG

LSSPVTKSFNRGEC.                                  214
```

```
Variable region: residues 1 to 107
                                        (SEQ ID NO: 4)
EIVMTQSPAILSLSPGERATLSCRASQSISDYLHWYQQKPGQAPRLLIKY
ASQSISGIPARFSGSGSGSDFTLTISSLQPEDFAVYYCQNGHSFPLTFGQ
GTKLEIK CDR1: residues 24 to 34
                                        (SEQ ID NO: 5)
RASQSISDYLH CDR2: residues 50 to 56
                                        (SEQ ID NO: 6)
YASQSIS CDR3: residues 89 to 97
                                        (SEQ ID NO: 7)
QNGHSFPLT CK: residues 108 to 214
```

T Cell Episcreen (Study 8)

The humanised antibody was further tested via in vitro T cell assays (Episcreen™) for its propensity to stimulate T cell activation, in comparison to the chimeric antibody. Bulk cultures of PBMC purified from normal human donors (selected to closely represent the distribution of HLA-DR in the world population) were stimulated with either a positive control, humanised antibody, chimeric antibody or media alone. On days 5 to 8, samples were removed and plated in replicate cultures in 96 well plates that were pulsed with tritiated thymidine. After 16 hours, proliferation was measured by scintillation counting and the test samples normalised to the media control to calculate a stimulation index (SI). Positive responses were defined as those where the test sample counts were significantly different from the media control. The results were benchmarked to a dataset consisting of a panel of molecules with known clinical immunogenicity that have previously been tested in the same assay. Result: the antibody displayed only very low levels of immunogenicity.

Competitive ELISA (Study 9)

A competitive Elisa was carried out to select the heavy and light chain combination that bound to recombinant human VCAM with the highest affinity and to ensure that no reduction in affinity was observed due to the humanisation process. Result: a comparable affinity was observed in the humanised antibody as compared to the original non humanised version.

Immunohistochemistry on TNF Stimulated and Non-Stimulated Human Vascular Endothelial Cells (Study 10)

Binding of HuVCAM-mMPIO to human VCAM-1 under static conditions: expression of human VCAM-1 was induced on HUVECs in culture by incubation with varying concentrations of TNF or without stimulation as a control. Binding was determined microscopically and quantified. Success was measured as binding of HuVCAM-mMPIO to the HUVECS. Result: the antibody displayed immunopositivity within TNF stimulated HUVECs known to upregulate VCAM, but not on unstimulated cells where no VCAM is expressed.

In more detail, expression of human VCAM-1 was induced on human umbilical vein endothelial cells (HUVECs) in culture by incubation with tumour necrosis factor (TNF). Binding of huVCAM-MPIO to the TNF-stimulated HUVECS was clearly evident (FIG. 1) and negligible on unstimulated HUVECs, with a 15-20-fold increase in binding events on the stimulated HUVECs. The huVCAM-mMPIO showed similar binding characteristics to the original murine VCAM-MPIO on murine endothelial cells.

Binding to Human Isolated Vessels (Study 11)

To assess whether our humanised antibody could recognise and bind to upregulated VCAM on isolated human brain microvessels under the shear and flow conditions that would be expected in the flowing blood, we covalently linked the antibody to commercial polystyrene beads and carried out a flow binding assay. Expression of human VCAM-1 was induced on HUVECs within a flow chamber by incubation with TNF. Success was measured on the basis of (a) standard shear curves, (b) numbers of attached and rolling mMPIO under constant shear perfusion, (c) rolling velocity measures and (d) binding vs HuVCAM-mMPIO concentration curves. Ideally the antibody would bind to VCAM under these physiological conditions. Result: the antibody recognised and bound to the activated VCAM on the human vessels.

In more detail, Binding of huVCAM-MPIO to activated human vessels was clearly observed, in both the presence and absence of TNF. Human coronary arteries (diameter: 100-150 μm) from right atrial appendages were dissected, cannulated and pressurized (80 mmHg). huVCAM-mMPIO were administered intraluminally at constant, pressure and perfusion flow rate (10 μl/min). Representative fluorescent (at 488 nm) images showed binding events of huVCAM-mMPIO before and after exposure to TNF (5 ng/ml, 4 h; n=4). Greater numbers of binding events (2-5 fold) were observed in TNF-stimulated vessels.

The invention claimed is:

1. A humanized antibody, or fragment thereof, comprising:
   a heavy chain that comprises from the heavy chain variable region of SEQ ID NO:10, at least a CDR1 comprising TSGLG from SEQ ID NO:11, a CDR2 comprising VYWDDDK from SEQ ID NO:12, and a CDR3 comprising RAFYGNNGAYAMDY from SEQ ID NO:13, and
   a light chain that comprises from the light chain variable region of SEQ ID NO:4 at least a CDR1 comprising QSISDY from SEQ ID NO:5, a CDR2 comprising YAS from SEQ ID NO:6, and a CDR3 comprising SEQ ID NO:7,
   wherein the antibody or fragment thereof specifically binds human endothelial vascular cell adhesion molecule 1 (VCAM-1).

2. An antibody or fragment thereof according to claim 1, wherein the antibody is a non-neutralising antibody.

3. An antibody according to claim 1, wherein said antibody has a low affinity between 1 to 500 μM Kd.

4. An antibody according to claim 1 wherein the antibody is a monoclonal antibody.

5. An antibody or fragment thereof according to claim 1, wherein the antibody or fragment thereof comprises:
   a light chain of SEQ ID NO: 3 or a light chain variable region amino acid sequence of SEQ ID NO: 4.

6. An antibody or fragment thereof according to claim 1, wherein the antibody comprises:
   (a) a heavy chain of SEQ ID NO: 9 or a heavy chain variable region amino acid sequence of SEQ ID NO: 10.

7. An antibody or fragment thereof according to claim 1, wherein the antibody comprises the light chain variable region of SEQ ID NO: 4 and the heavy chain variable region of SEQ ID NO: 10.

8. An antibody or fragment thereof according to claim 1, wherein the antibody comprises a light chain of SEQ ID NO: 3 and the heavy chain of SEQ ID NO: 9.

9. An antibody or fragment according to claim 1 wherein the antibody is conjugated to an iron oxide microparticle.

10. An antibody or fragment thereof according to claim 9, wherein the antibody is conjugated to an iron oxide microparticle which is covalently bonded to other iron oxide microparticles by cleavable linker groups to form a multimeric particle.

11. An antibody or fragment thereof according to claim 1, wherein the antibody binds to the extracellular domain of VCAM-1.

12. An antibody or fragment thereof according to claim 1, wherein the antibody binds to VCAM-1 when expressed on endothelial cells.

13. A composition comprising the antibody or fragment thereof according to claim 1.

14. The composition of claim 13, wherein the antibody or fragment thereof is formulated in a pharmaceutically acceptable carrier.

* * * * *

SEQUENCE LISTING

```
<160> NUMBER OF SEQ ID NOS: 13

<210> SEQ ID NO 1
<211> LENGTH: 674
<212> TYPE: PRT
<213> ORGANISM: Homo sapiens

<400> SEQUENCE: 1

Phe Lys Ile Glu Thr Thr Pro Glu Ser Arg Tyr Leu Ala Gln Ile Gly
1               5                   10                  15

Asp Ser Val Ser Leu Thr Cys Ser Thr Thr Gly Cys Glu Ser Pro Phe
            20                  25                  30

Phe Ser Trp Arg Thr Gln Ile Asp Ser Pro Leu Asn Gly Lys Val Thr
        35                  40                  45

Asn Glu Gly Thr Thr Ser Thr Leu Thr Met Asn Pro Val Ser Phe Gly
    50                  55                  60

Asn Glu His Ser Tyr Leu Cys Thr Ala Thr Cys Glu Ser Arg Lys Leu
65                  70                  75                  80

Glu Lys Gly Ile Gln Val Glu Ile Tyr Ser Phe Pro Lys Asp Pro Glu
                85                  90                  95

Ile His Leu Ser Gly Pro Leu Glu Ala Gly Lys Pro Ile Thr Val Lys
            100                 105                 110

Cys Ser Val Ala Asp Val Tyr Pro Phe Asp Arg Leu Glu Ile Asp Leu
        115                 120                 125

Leu Lys Gly Asp His Leu Met Lys Ser Gln Glu Phe Leu Glu Asp Ala
    130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
            180                 185                 190

Leu Gln Val Tyr Ile Ser Pro Lys Asn Thr Val Ile Ser Val Asn Pro
        195                 200                 205

Ser Thr Lys Leu Gln Glu Gly Gly Ser Val Thr Met Thr Cys Ser Ser
    210                 215                 220

Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
```

```
                275                 280                 285
        Phe Thr Val Glu Ile Ser Pro Gly Pro Arg Ile Ala Ala Gln Ile Gly
        290                 295                 300

Asp Ser Val Met Leu Thr Cys Ser Val Met Gly Cys Glu Ser Pro Ser
    305                 310                 315                 320

Phe Ser Trp Arg Thr Gln Ile Asp Ser Pro Leu Ser Gly Lys Val Arg
                        325                 330                 335

Ser Glu Gly Thr Asn Ser Thr Leu Thr Leu Ser Pro Val Ser Phe Glu
                        340                 345                 350

Asn Glu His Ser Tyr Leu Cys Thr Val Thr Cys Gly His Lys Lys Leu
                        355                 360                 365

Glu Lys Gly Ile Gln Val Glu Leu Tyr Ser Phe Pro Arg Asp Pro Glu
                        370                 375                 380

Ile Glu Met Ser Gly Gly Leu Val Asn Gly Ser Ser Val Thr Val Ser
    385                 390                 395                 400

Cys Lys Val Pro Ser Val Tyr Pro Leu Asp Arg Leu Glu Ile Glu Leu
                        405                 410                 415

Leu Lys Gly Glu Thr Ile Leu Glu Asn Ile Glu Phe Leu Glu Asp Thr
                        420                 425                 430

Asp Met Lys Ser Leu Glu Asn Lys Ser Leu Glu Met Thr Phe Ile Pro
                        435                 440                 445

Thr Ile Glu Asp Thr Gly Lys Ala Leu Val Cys Gln Ala Lys Leu His
    450                 455                 460

Ile Asp Asp Met Glu Phe Glu Pro Lys Gln Arg Gln Ser Thr Gln Thr
    465                 470                 475                 480

Leu Tyr Val Asn Val Ala Pro Arg Asp Thr Thr Val Leu Val Ser Pro
                        485                 490                 495

Ser Ser Ile Leu Glu Glu Gly Ser Ser Val Asn Met Thr Cys Leu Ser
                        500                 505                 510

Gln Gly Phe Pro Ala Pro Lys Ile Leu Trp Ser Arg Gln Leu Pro Asn
                        515                 520                 525

Gly Glu Leu Gln Pro Leu Ser Glu Asn Ala Thr Leu Thr Leu Ile Ser
                        530                 535                 540

Thr Lys Met Glu Asp Ser Gly Val Tyr Leu Cys Glu Gly Ile Asn Gln
    545                 550                 555                 560

Ala Gly Arg Ser Arg Lys Glu Val Glu Leu Ile Ile Gln Val Thr Pro
                        565                 570                 575

Lys Asp Ile Lys Leu Thr Ala Phe Pro Ser Glu Ser Val Lys Glu Gly
                        580                 585                 590

Asp Thr Val Ile Ile Ser Cys Thr Cys Gly Asn Val Pro Glu Thr Trp
                        595                 600                 605

Ile Ile Leu Lys Lys Lys Ala Glu Thr Gly Asp Thr Val Leu Lys Ser
                        610                 615                 620

Ile Asp Gly Ala Tyr Thr Ile Arg Lys Ala Gln Leu Lys Asp Ala Gly
    625                 630                 635                 640

Val Tyr Glu Cys Glu Ser Lys Asn Lys Val Gly Ser Gln Leu Arg Ser
                        645                 650                 655

Leu Thr Leu Asp Val Gln Gly Arg Glu Asn Asn Lys Asp Tyr Phe Ser
                        660                 665                 670

Pro Glu

<210> SEQ ID NO 2
<211> LENGTH: 1018
```

<212> TYPE: DNA
<213> ORGANISM: Artificial Sequence
<220> FEATURE:
<223> OTHER INFORMATION: Humanised antibody sequence
<220> FEATURE:
<221> NAME/KEY: CDS
<222> LOCATION: (1)..(322)
<220> FEATURE:
<221> NAME/KEY: CDS
<222> LOCATION: (699)..(1018)

<400> SEQUENCE: 2

```
gag att gtg atg act cag tct cca gcc acc cta tct ctg tct cca gga         48
Glu Ile Val Met Thr Gln Ser Pro Ala Thr Leu Ser Leu Ser Pro Gly
1               5                  10                  15 gag aga gcc act ctt tcc tgc agg gcc agt cag agt att agc gac tac         96
Glu Arg Ala Thr Leu Ser Cys Arg Ala Ser Gln Ser Ile Ser Asp Tyr
            20                  25                  30 tta cac tgg tat caa caa aaa cca ggc cag gct ccg agg ctt ctc atc        144
Leu His Trp Tyr Gln Gln Lys Pro Gly Gln Ala Pro Arg Leu Leu Ile
        35                  40                  45 aaa tat gct tcc caa tcc atc tct ggc atc ccc gcc agg ttc agt ggc        192
Lys Tyr Ala Ser Gln Ser Ile Ser Gly Ile Pro Ala Arg Phe Ser Gly
    50                  55                  60 agt gga tca ggg tca gat ttc act ctc act atc agc agt ctg cag cct        240
Ser Gly Ser Gly Ser Asp Phe Thr Leu Thr Ile Ser Ser Leu Gln Pro
65                  70                  75                  80 gaa gat ttt gca gtg tat tac tgt caa aat ggt cac agc ttt ccg ctc        288
Glu Asp Phe Ala Val Tyr Tyr Cys Gln Asn Gly His Ser Phe Pro Leu
                85                  90                  95 acg ttc ggt cag ggg acc aag ctg gag atc aaa c gtgagtagaa               332
Thr Phe Gly Gln Gly Thr Lys Leu Glu Ile Lys
            100                 105 tttaaacttt gcttcctcag ttggatcccg caattctaaa ctctgagggg gtcggatgac      392
gtggccattc tttgcctaaa gcattgagtt tactgcaagg tcagaaaagc atgcaaagcc      452
ctcagaatgg ctgcaaagag ctccaacaaa acaatttaga actttattaa ggaatagggg      512
gaagctagga agaaactcaa acatcaagat ttttaaatac gcttcttggt ctccttgcta      572
taattatctg ggataagcat gctgttttct gtctgtccct aacatgccct gtgattatcc      632
gcaaacaaca cacccaaggg cagaactttg ttacttaaac accatcctgt ttgcttcttt      692 cctcag ga  act gtg gct gca cca tct gtc ttc atc ttc ccg cca tct        739
           Arg Thr Val Ala Ala Pro Ser Val Phe Ile Phe Pro Pro Ser
               110                 115                 120 gat gag cag ttg aaa tct gga act gcc tct gtt gtg tgc ctg ctg aat        787
Asp Glu Gln Leu Lys Ser Gly Thr Ala Ser Val Val Cys Leu Leu Asn
        125                 130                 135 aac ttc tat ccc aga gag gcc aaa gta cag tgg aag gtg gat aac gcc        835
Asn Phe Tyr Pro Arg Glu Ala Lys Val Gln Trp Lys Val Asp Asn Ala
    140                 145                 150 ctc caa tcg ggt aac tcc cag gag agt gtc aca gag cag gac agc aag        883
Leu Gln Ser Gly Asn Ser Gln Glu Ser Val Thr Glu Gln Asp Ser Lys
155                 160                 165 gac agc acc tac agc ctc agc agc acc ctg acg ctg agc aaa gca gac        931
Asp Ser Thr Tyr Ser Leu Ser Ser Thr Leu Thr Leu Ser Lys Ala Asp
170                 175                 180                 185 tac gag aaa cac aaa gtc tac gcc tgc gaa gtc acc cat cag ggc ctg        979
Tyr Glu Lys His Lys Val Tyr Ala Cys Glu Val Thr His Gln Gly Leu
                190                 195                 200 agc tcg ccc gtc aca aag agc ttc aac agg gga gag tgt                   1018
Ser Ser Pro Val Thr Lys Ser Phe Asn Arg Gly Glu Cys
```

-continued

```
                    205                 210

<210> SEQ ID NO 3
<211> LENGTH: 214
<212> TYPE: PRT
<213> ORGANISM: Artificial Sequence
<220> FEATURE:
<223> OTHER INFORMATION: Humanised antibody sequence

<400> SEQUENCE: 3

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Ser Asp Phe Thr Leu Thr Ile Ser Ser Leu Gln Pro
65                  70                  75                  80

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 107
<212> TYPE: PRT
<213> ORGANISM: Artificial Sequence
<220> FEATURE:
<223> OTHER INFORMATION: Humanised antibody sequence

<400> SEQUENCE: 4

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Ser Asp Phe Thr Leu Thr Ile Ser Ser Leu Gln Pro
65                  70                  75                  80
```

Glu Asp Phe Ala Val Tyr Tyr Cys Gln Asn Gly His Ser Phe Pro Leu
                85                  90                  95

Thr Phe Gly Gln Gly Thr Lys Leu Glu Ile Lys
            100                 105

<210> SEQ ID NO 5
<211> LENGTH: 11
<212> TYPE: PRT
<213> ORGANISM: Artificial Sequence
<220> FEATURE:
<223> OTHER INFORMATION: Humanised antibody sequence

<400> SEQUENCE: 5

Arg Ala Ser Gln Ser Ile Ser Asp Tyr Leu His
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Humanised antibody sequence

<400> SEQUENCE: 6

Tyr Ala Ser Gln Ser Ile Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Humanised antibody sequence

<400> SEQUENCE: 7

Gln Asn Gly His Ser Phe Pro Leu Thr
1               5

<210> SEQ ID NO 8
<211> LENGTH: 2178
<212> TYPE: DNA
<213> ORGANISM: Artificial Sequence
<220> FEATURE:
<223> OTHER INFORMATION: Humanised antibody sequence
<220> FEATURE:
<221> NAME/KEY: CDS
<222> LOCATION: (1)..(373)
<220> FEATURE:
<221> NAME/KEY: CDS
<222> LOCATION: (592)..(885)
<220> FEATURE:
<221> NAME/KEY: CDS
<222> LOCATION: (1278)..(1313)
<220> FEATURE:
<221> NAME/KEY: CDS
<222> LOCATION: (1432)..(1761)
<220> FEATURE:
<221> NAME/KEY: CDS
<222> LOCATION: (1859)..(2178)

<400> SEQUENCE: 8 cag gtt act ctg aaa gag tct ggc cct gcc ctg gtg aag ccc acc cag      48
Gln Val Thr Leu Lys Glu Ser Gly Pro Ala Leu Val Lys Pro Thr Gln
1               5                   10                  15 acc ctc act ctg act tgt tct ttc tct ggg ttt tca ctg agc act tct      96
Thr Leu Thr Leu Thr Cys Ser Phe Ser Gly Phe Ser Leu Ser Thr Ser
            20                  25                  30 ggt ttg ggt gtg agc tgg att cgt cag cct tca gga aag gct ctg gag     144

```
                 Gly Leu Gly Val Ser Trp Ile Arg Gln Pro Ser Gly Lys Ala Leu Glu
                              35                  40                  45 tgg ctg gca cac gtt tac tgg gat gat gac aag ctc tat aac cca tcc          192
Trp Leu Ala His Val Tyr Trp Asp Asp Asp Lys Leu Tyr Asn Pro Ser
         50                  55                  60 ctg aag agt cgg ctc aca atc tcc aag gat acc tcc aaa aac cag gta          240
Leu Lys Ser Arg Leu Thr Ile Ser Lys Asp Thr Ser Lys Asn Gln Val
 65                  70                  75                  80 gtc ctc acc atg acc aat atg gac cct gtg gat act gcc aca tac tac          288
Val Leu Thr Met Thr Asn Met Asp Pro Val Asp Thr Ala Thr Tyr Tyr
                         85                  90                  95 tgt ggt cga aga gcc ttc tat ggt aac aac ggg gcc tat gct atg gac          336
Cys Gly Arg Arg Ala Phe Tyr Gly Asn Asn Gly Ala Tyr Ala Met Asp
                100                 105                 110 tac tgg ggt caa gga acc ctg gtc acc gtc tcc tca g gtaagctttc             383
Tyr Trp Gly Gln Gly Thr Leu Val Thr Val Ser Ser
        115                 120 tggggcaggc cgggcctgac tttggctggg ggcaggagg gggctaaggt gacgcaggtg         443
gcgccagcca ggtgcacacc caatgcccat gagcccagac actggaccct gcatggacca       503
tcgcggatag acaagaaccg aggggcctct gcgccctggg cccagctctg tcccacaccg       563
cggtcacatg gcaccacctc tcttgcag ct  tcc acc aag ggc cca tcc gtc          614
                                  Ala Ser Thr Lys Gly Pro Ser Val
                                             125                 130 ttc ccc ctg gcg ccc tgc tcc agg agc acc tcc gag agc aca gcc gcc         662
Phe Pro Leu Ala Pro Cys Ser Arg Ser Thr Ser Glu Ser Thr Ala Ala
             135                 140                 145 ctg ggc tgc ctg gtc aag gac tac ttc ccc gaa ccg gtg acg gtg tcg         710
Leu Gly Cys Leu Val Lys Asp Tyr Phe Pro Glu Pro Val Thr Val Ser
    150                 155                 160 tgg aac tca ggc gcc ctg acc agc ggc gtg cac acc ttc ccg gct gtc         758
Trp Asn Ser Gly Ala Leu Thr Ser Gly Val His Thr Phe Pro Ala Val
165                 170                 175                 180 cta cag tcc tca gga ctc tac tcc ctc agc agc gtg gtg acc gtg ccc         806
Leu Gln Ser Ser Gly Leu Tyr Ser Leu Ser Ser Val Val Thr Val Pro
                185                 190                 195 tcc agc agc ttg ggc acg aag acc tac acc tgc aat gta gat cac aag         854
Ser Ser Ser Leu Gly Thr Lys Thr Tyr Thr Cys Asn Val Asp His Lys
            200                 205                 210 ccc agc aac acc aag gtg gac aag aga gtt g gtgagaggcc agcacaggga         905
Pro Ser Asn Thr Lys Val Asp Lys Arg Val
        215                 220 gggagggtgt ctgctggaag ccaggctcag ccctcctgcc tggacgcacc ccggctgtgc       965
agccccagcc cagggcagca aggcaggccc catctgtctc ctcacctgga ggcctctgac      1025 cacccccactc atgctcaggg agagggtctt ctggattttt ccaccaggct ccgggcagcc     1085
acaggctgga tgcccctacc ccaggccctg cgcatacagg ggcaggtgct gcgctcagac      1145
ctgccaagag ccatatccgg gaggaccctg ccctgacct aagcccaccc caaaggccaa       1205
actctccact ccctcagctc agacaccttc tctcctccca gatctgagta actcccaatc     1265
ttctctctgc ag ag  tcc aaa tat ggt ccc cca tgc cca cca tgc cca g         1313
               Glu Ser Lys Tyr Gly Pro Pro Cys Pro Pro Cys Pro
                        225                 230 gtaagccaac ccaggcctcg ccctccagct caaggcggga caggtgccct agagtagcct     1373
gcatccaggg acaggcccca gccgggtgct gacgcatcca cctccatctc ttcctcag       1431 ca  cct gag ttc ctg ggg gga cca tca gtc ttc ctg ttc ccc cca aaa        1478
Ala Pro Glu Phe Leu Gly Gly Pro Ser Val Phe Leu Phe Pro Pro Lys
```

-continued

```
                235                 240                 245                 250 ccc aag gac act ctc atg atc tcc cgg acc cct gag gtc acg tgc gtg         1526
Pro Lys Asp Thr Leu Met Ile Ser Arg Thr Pro Glu Val Thr Cys Val
                255                 260                 265 gtg gtg gac gtg agc cag gaa gac ccc gag gtc cag ttc aac tgg tac         1574
Val Val Asp Val Ser Gln Glu Asp Pro Glu Val Gln Phe Asn Trp Tyr
                270                 275                 280 gtg gat ggc gtg gag gtg cat aat gcc aag aca aag ccg cgg gag gag         1622
Val Asp Gly Val Glu Val His Asn Ala Lys Thr Lys Pro Arg Glu Glu
            285                 290                 295 cag ttc aac agc acg tac cgt gtg gtc agc gtc ctc acc gtc ctg cac         1670
Gln Phe Asn Ser Thr Tyr Arg Val Val Ser Val Leu Thr Val Leu His
        300                 305                 310 cag gac tgg ctg aac ggc aag gag tac aag tgc aag gtc tcc aac aaa         1718
Gln Asp Trp Leu Asn Gly Lys Glu Tyr Lys Cys Lys Val Ser Asn Lys
315                 320                 325                 330 ggc ctc ccg tcc tcc atc gag aaa acc atc tcc aaa gcc aaa g               1761
Gly Leu Pro Ser Ser Ile Glu Lys Thr Ile Ser Lys Ala Lys
                335                 340 gtgggaccca cggggtgcga gggccacatg gacagaggtc agctcggccc accctctgcc       1821
ctgggagtga ccgctgtgcc aacctctgtc cctacag gg  cag ccc cga gag cca        1875
                                            Gly Gln Pro Arg Glu Pro
                                                345                 350 cag gtg tac acc ctg ccc cca tcc cag gag gag atg acc aag aac cag         1923
Gln Val Tyr Thr Leu Pro Pro Ser Gln Glu Glu Met Thr Lys Asn Gln
                355                 360                 365 gtc agc ctg acc tgc ctg gtc aaa ggc ttc tac ccc agc gac atc gcc         1971
Val Ser Leu Thr Cys Leu Val Lys Gly Phe Tyr Pro Ser Asp Ile Ala
            370                 375                 380 gtg gag tgg gag agc aat ggg cag ccg gag aac aac tac aag acc acg         2019
Val Glu Trp Glu Ser Asn Gly Gln Pro Glu Asn Asn Tyr Lys Thr Thr
        385                 390                 395 cct ccc gtg ctg gac tcc gac ggc tcc ttc ttc ctc tac agc agg cta         2067
Pro Pro Val Leu Asp Ser Asp Gly Ser Phe Phe Leu Tyr Ser Arg Leu
    400                 405                 410 acc gtg gac aag agc agg tgg cag gag ggg aat gtc ttc tca tgc tcc         2115
Thr Val Asp Lys Ser Arg Trp Gln Glu Gly Asn Val Phe Ser Cys Ser
415                 420                 425                 430 gtg atg cat gag gct ctg cac aac cac tac aca cag aag agc ctc tcc         2163
Val Met His Glu Ala Leu His Asn His Tyr Thr Gln Lys Ser Leu Ser
                435                 440                 445 ctg tct ctg ggt aaa                                                     2178
Leu Ser Leu Gly Lys
            450

<210> SEQ ID NO 9
<211> LENGTH: 451
<212> TYPE: PRT
<213> ORGANISM: Artificial Sequence
<220> FEATURE:
<223> OTHER INFORMATION: Humanised antibody sequence

<400> SEQUENCE: 9

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Leu Gly Val Ser Trp Ile Arg Gln Pro Ser Gly Lys Ala Leu Glu
        35                  40                  45
```

```
Trp Leu Ala His Val Tyr Trp Asp Asp Asp Lys Leu Tyr Asn Pro Ser
    50              55                  60
Leu Lys Ser Arg Leu Thr Ile Ser Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Gly Arg Arg Ala Phe Tyr Gly Asn Asn Gly Ala Tyr Ala Met Asp
            100                 105                 110
Tyr Trp Gly Gln Gly Thr Leu Val Thr Val Ser Ser Ala Ser Thr Lys
        115                 120                 125
Gly Pro Ser Val Phe Pro Leu Ala Pro Cys Ser Arg Ser Thr Ser Glu
    130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Lys Thr Tyr Thr Cys Asn
        195                 200                 205
Val Asp His Lys Pro Ser Asn Thr Lys Val Asp Lys Arg Val Glu Ser
    210                 215                 220
Lys Tyr Gly Pro Pro Cys Pro Pro Cys Pro Ala Pro Glu Phe Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser Gln
            260                 265                 270
Glu Asp Pro Glu Val Gln Phe Asn Trp Tyr Val Asp Gly Val Glu Val
        275                 280                 285
His Asn Ala Lys Thr Lys Pro Arg Glu Glu Gln Phe Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Gln Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
            420                 425                 430
His Glu Ala Leu His Asn His Tyr Thr Gln Lys Ser Leu Ser Leu Ser
        435                 440                 445
Leu Gly Lys
    450
```

```
<210> SEQ ID NO 10
<211> LENGTH: 124
<212> TYPE: PRT
<213> ORGANISM: Artificial Sequence
<220> FEATURE:
<223> OTHER INFORMATION: Humanised antibody sequence

<400> SEQUENCE: 10

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Leu Gly Val Ser Trp Ile Arg Gln Pro Ser Gly Lys Ala Leu Glu
        35                  40                  45

Trp Leu Ala His Val Tyr Trp Asp Asp Asp Lys Leu Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Gly Arg Arg Ala Phe Tyr Gly Asn Asn Gly Ala Tyr Ala Met Asp
            100                 105                 110

Tyr Trp Gly Gln Gly Thr Leu Val Thr Val Ser Ser
        115                 120

<210> SEQ ID NO 11
<211> LENGTH: 7
<212> TYPE: PRT
<213> ORGANISM: Artificial Sequence
<220> FEATURE:
<223> OTHER INFORMATION: Humanised antibody sequence

<400> SEQUENCE: 11

Thr Ser Gly Leu Gly Val Ser
1               5

<210> SEQ ID NO 12
<211> LENGTH: 16
<212> TYPE: PRT
<213> ORGANISM: Artificial Sequence
<220> FEATURE:
<223> OTHER INFORMATION: Humanised antibody sequence

<400> SEQUENCE: 12

His Val Tyr Trp Asp Asp Asp Lys Leu Tyr Asn Pro Ser Leu Lys Ser
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Humanised antibody sequence

<400> SEQUENCE: 13

Arg Ala Phe Tyr Gly Asn Asn Gly Ala Tyr Ala Met Asp Tyr
1               5                   10
```